(12) United States Patent
Matt

(10) Patent No.: US 12,004,867 B2
(45) Date of Patent: Jun. 11, 2024

(54) THREE DIMENSIONAL IMAGING OF THE MOTION OF TEETH AND JAWS

(71) Applicant: Shane Matt, Austin, TX (US)

(72) Inventor: Shane Matt, Austin, TX (US)

( * ) Notice: Subject to any disclaimer, the term of this patent is extended or adjusted under 35 U.S.C. 154(b) by 86 days.

(21) Appl. No.: 14/934,060

(22) Filed: Nov. 5, 2015

(65) Prior Publication Data

US 2016/0128624 A1    May 12, 2016

Related U.S. Application Data

(60) Provisional application No. 62/075,934, filed on Nov. 6, 2014.

(51) Int. Cl.
| | | |
|---|---|---|
| *A61B 5/00* | (2006.01) | |
| *A61B 5/0205* | (2006.01) | |
| *A61B 5/11* | (2006.01) | |
| *A61C 7/00* | (2006.01) | |
| *A61C 19/045* | (2006.01) | |
| *A61B 5/055* | (2006.01) | |
| *A61B 6/51* | (2024.01) | |
| *A61B 8/08* | (2006.01) | |
| *A61F 5/56* | (2006.01) | |

(52) U.S. Cl.
CPC .......... *A61B 5/4542* (2013.01); *A61B 5/0073* (2013.01); *A61B 5/0205* (2013.01); *A61B 5/1128* (2013.01); *A61B 5/4557* (2013.01); *A61C 7/002* (2013.01); *A61C 19/045* (2013.01); *A61B 5/055* (2013.01); *A61B 6/51* (2024.01); *A61B 8/0875* (2013.01); *A61B 2560/0223* (2013.01); *A61B 2562/0219* (2013.01); *A61B 2562/0223* (2013.01); *A61F 2005/563* (2013.01)

(58) Field of Classification Search
CPC .......... A61B 2562/0219; A61B 5/4542; A61C 19/045; A61C 7/002
See application file for complete search history.

(56) References Cited

U.S. PATENT DOCUMENTS

| | | |
|---|---|---|
| 3,259,984 A | 7/1966 | Seidenberg |
| 4,344,441 A | 8/1982 | Radke |
| (Continued) | | |

FOREIGN PATENT DOCUMENTS

WO    WO 2013/192582 A1    12/2013

OTHER PUBLICATIONS

Todd Shewman, 3-Dimensional Physiologic Postural Range of the Mandible: A Computerized-Assisted Technique—A Case Study, Case Reports in Medicine vol. 2013, Article ID 698397, 11 pages, http://dx.doi.org/10.1155/2013/698397.*

(Continued)

*Primary Examiner* — Scott Luan
(74) *Attorney, Agent, or Firm* — Gregory K. Goshorn; GREG GOSHORN, P.C.

(57) ABSTRACT

Pre-calibrated position sensors, and a computer or cloud based service are used to show motion in real time of the teeth and jaws depicting six degrees of freedom. The computer receives anatomically correct 3D images of any portion of the craniomandibular system with a position sensor(s) attached. The position sensor data is then transferred with wireless attachments to the patient to generate true to life motion of the digital 3D models of the teeth and jaws. The 3D models are then employed to provide various techniques for treating bite disorders.

30 Claims, 10 Drawing Sheets

(56) References Cited

U.S. PATENT DOCUMENTS

| | | | |
|---|---|---|---|
| 4,447,207 A | 5/1984 | Kataoka et al. | |
| 4,765,345 A | 8/1988 | Adib | |
| 4,837,685 A | 6/1989 | Jokela | |
| 5,826,579 A | 10/1998 | Remmers et al. | |
| 5,989,023 A | 11/1999 | Summer et al. | |
| 7,402,996 B2 | 7/2008 | Arai et al. | |
| 8,013,853 B1 | 9/2011 | Douglas et al. | |
| 8,037,886 B2 | 10/2011 | Sotos et al. | |
| 8,226,407 B2 | 7/2012 | Hanewinkel et al. | |
| 8,382,686 B2 | 2/2013 | Gutman et al. | |
| 8,544,322 B2 | 10/2013 | Minami et al. | |
| 8,550,816 B2 | 10/2013 | Hanewinkel et al. | |
| 8,562,340 B2 | 10/2013 | Chishti et al. | |
| 8,578,937 B2 | 11/2013 | Bhat et al. | |
| 8,594,408 B2 | 11/2013 | Alpern et al. | |
| 8,620,045 B2 | 12/2013 | Adams | |
| 8,667,972 B2 | 3/2014 | Makkar et al. | |
| 8,671,946 B2 | 3/2014 | Thornton | |
| 8,734,150 B2 | 5/2014 | Chishti et al. | |
| 8,794,962 B2 | 8/2014 | Lauren | |
| 8,875,713 B2 | 11/2014 | Metz | |
| 9,561,088 B2 | 2/2017 | Sachdeva et al. | |
| 9,888,983 B2 | 2/2018 | Sachdeva et al. | |
| 9,895,120 B2 | 2/2018 | Nyholm et al. | |
| 10,124,236 B2 | 11/2018 | Mohler | |
| 10,166,091 B2 | 1/2019 | Cowburn et al. | |
| 10,172,548 B2 | 1/2019 | Remmers et al. | |
| 10,228,428 B2 | 3/2019 | Gustafsson et al. | |
| 2006/0018844 A1 | 1/2006 | Katz et al. | |
| 2007/0252586 A1* | 11/2007 | Arai | A61B 5/1126 324/207.13 |
| 2009/0179986 A1 | 7/2009 | Klett | |
| 2010/0239996 A1* | 9/2010 | Ertl | A61B 6/145 433/29 |
| 2012/0015316 A1 | 1/2012 | Sachdeva et al. | |
| 2012/0022844 A1* | 1/2012 | Teixeira | A61B 5/0205 703/11 |
| 2012/0107763 A1* | 5/2012 | Adams | A61B 1/24 433/29 |
| 2012/0115107 A1 | 5/2012 | Adams | |
| 2015/0174418 A1 | 6/2015 | Tyler et al. | |
| 2015/0305669 A1* | 10/2015 | Hultgren | A61B 5/4547 433/27 |

OTHER PUBLICATIONS

International Search Authoprity, "International Search Report," dated Feb. 2, 2016.

European Patent Office, "Extended European Search Report," dated Apr. 26, 2018.

Akyalcin et al.; 2013, "Diagnostic accuracy of impression-free digital models"; Am J Orthod Dentofacial Orthop., v. 144, p. 916-922, PMID: 24286915; downloaded from <https://www.ajodo.org/article/S0889-5406(13)00832-9/abstract> on Apr. 1, 2019; 2013.

Ender; "Influence of scanning strategies on the accuracy of digital intraoral scanning systems", Int J Comput Dent., v. 16, p. 11-21; PMID: 23641661; downloaded from <https://www.ncbi.nlm.nih.gov/pubmed/23641661> on Apr. 1, 2019; 2013.

Uchida et al., "Studies evaluating measurement accuracy of CMS-JAW, a jaw motion tracking device with six degrees of freedom using an ultrasonic recording system," Nihon Hotetsu Shika Gakkai Zasshi, v. 52, p. 350-359, PMID: 18678968; downloaded from <https://www.ncbi.nlm.nih.gov/pubmed/18678968. on Apr. 1, 2019; 2003.

Xia et al.; "A new method to orient 3-dimensional computed tomography models to the natural head position: a clinical feasibility study"; J Oral Maxillofac Surg., v. 69, p. 584-591, PMID: 21353923; downloaded from <https://www.ncbi.nlm.nih.gov/pubmed/21353923> on Apr. 1, 2019; 2011.

Dort et al.; "Mandibular advancement and obstructive sleep apnea: a method for determining effective mandibular protrusion"; Eur Respir J., v. 27, p. 1003-1009; PMID: 16707396; downloaded from <https://www.ncbi.nlm.nih.gov/pubmed/16707396> on Apr. 1, 2019; 2006.

Remmers et al.; "Remotely controlled mandibular protrusion during sleep predicts therapeutic success with oral appliances in patients with obstructive sleep apnea"; Sleep, v. 36, p. 1517-1525; PMID: 24082311; downloaded from <https://www.ncbi.nlm.nih.gov/pubmed/24082311> on Apr. 1, 2019; 2013.

Cunali et al.; "Prevalence of temporomandibular disorders in obstructive sleep apnea patients referred for oral appliance therapy"; J Orofac Pain. 2009 Fall; 23(4):339-44downloaded from <https://www.ncbi.nlm.nih.gov/pubmed/19888485> on Apr. 1, 2019; 2009.

Sutherland et al.; "Oral Appliance Treatment for Obstructive Sleep Apnea: An Update"; JOPurnal of Clinical Sleep Medicine, V. 10, No. 2, pp. 215-227; 2014.

American Sleep Disorders Association; "Practice Parameters for the Treatment of Snoring and Obstructive Sleep Apnea with Oral Appliances"; Sleep, V. 18, No. 6, pp. 511-513; 1995.

American Sleep Disorders Association; "Oral Appliances for the Treatment of Snoring and Obstructive Sleep Apnea: A Review"; Sleep, V. 18, No. 6, pp. 501-510; 1995.

Zebris Medical GmbH, "Measuring the lower jaw easily and precisely"; downloaded from <https://www.zebris.de/en/dental/products-solutions/jaw-registration-jmanalyser/> on Apr. 2, 2019.

Smith et al.; "Evaluation of a Novel Device for Measuring Patient Compliance with Oral Appliances in the Treatment of Obstructive Sleep Apnea" J Prosthodont, [Epub ahead of print], PMID: 23889695; downloaded from <https://www.ncbi.nlm.nih.gov/pubmed/23889695> on Apr. 3, 2019; 2013.

Missaka et al.; "Development of an experimental optoelectronic device to study the amplitude of mandibular movements"; Braz Oral Res., v. 22, p. 151-157, PMID: 18622485; downloaded from <http://www.scielo.br/pdf/bor//22n2/10.pdf> on Apr. 3, 2019; 2008.

Liu et al.; "Establishment and accuracy examination of gyroscope for recording and transferring natural head position"; Beijing Da Xue Xue Bao., v. 46, p. 86-89, PMID: 24535355; downloaded from <https://www.ncbi.nlm.nih.gov/pubmed/24535355> on Apr. 3, 2019; 2014.

* cited by examiner

THREE DIMENSIONAL IMAGING OF THE MOTION OF TEETH AND JAWS

CROSS-REFERENCES TO RELATED APPLICATIONS

The present application claims the benefit of the filing date of a provisional application entitled, "Three Dimensional Imaging of the Motion of Teeth and Jaws" Ser. No. 62/075,934, filed Nov. 6, 2014.

FIELD OF THE DISCLOSURE

The claimed subject matter relates generally to the generation of three dimensional (3D) imaging of the teeth and jaws and, more specifically, with the capture of 3D images and various techniques that utilize the 3D imaging.

BACKGROUND

The human jaw and its associated structures are one of the most highly innervated areas of the body. The jawbone exhibits the most complex movements in the body. Operating with six degrees of freedom, it is the only bilateral functioning bone with Temporomandibular Joints (TMJ) on each side. Dysfunction in one joint can affect the opposite joint. Temporomandibular Joint Dysfunction (TMD) typically begins with a breakdown of the soft tissues in the joint due to displacement of the joint disc. As the joint breaks down, noises can be recorded and analyzed to determine the extent of damage. Those so affected may experience a partial inability to open the mouth and even extreme pain that may be referred to muscles or teeth. One of the biggest hurdles in comprehensive care for dentistry is in the diagnosis and treatment of jaw joint and bite dysfunctions.

It is not only the TMJ that is of concern. More comprehensively known as craniomandibular dysfunction, other signs and symptoms include head and neck pain, dental pain, worn, broken or mal-aligned teeth, bruxism (grinding teeth) among many others. Even sleep apnea is associated jaw issues. A patent airway is the most critical issue for survival. Chronic partial obstruction from sleep apnea can lead to numerous systemic health problems most adversely being with the heart. There is not currently an affordable comprehensive system that displays the relationship between these health problems and successful treatment.

Current diagnostic modalities for jaw dysfunctions include magnetic resonance imaging (MRI); computed tomography (CT); radiographs; sonography; jaw tracking; electromyogram (EMG); digital photography; and exact replica, mounted models of the teeth. This information, usually gathered at different times and locations, is used to formulate a diagnosis and treatment, often resulting in a slow, difficult and expensive process. Moreover, the previously known techniques only give physicians a three-dimensional graphic of a single point tracing, a limitation that makes it difficult to fully evaluate and understand the technical problems to be addressed, especially given the jaw's six-dimensional pitch, roll and yaw.

Another commonly prescribed imaging option is radiography. Corrected tomography is significantly less expensive than MRI/CT, but the quality is substandard. Like CTs there is no visualization of the soft tissue. One may see the position of the jaw in the joint, but can only mentally visualize the status of the soft tissues. Advantages of tomography are that it is an affordable office option, and can be useful in analyzing arthritic changes of the bone.

Many methods and devices have been described for tracking mandibular motion. Devices include video tracking, ultrasound and more commonly, various magnetic systems. One such magnetic system is achieved with a sensory array that tracks a magnet attached to the lower front teeth. The magnet movement is graphically depicted on-screen in real-time, and dysfunction in the joints can be deduced by analyzing the tracing.

For example, an internal derangement in the right joint will result in a deviation to the right until the joint disc is recaptured, and the jaw moves back toward the midline. If the derangement is in both joints and the joint disc cannot be recaptured there will be limited opening. The integrity of the soft tissue in function remains a mystery, although audio joint sonography gives some insight. A spectral analysis of the frequencies emitted during joint function reveals whether there is soft tissue damage or if there is bone on bone contact.

SUMMARY

Pre-calibrated position sensors, and a computer or cloud based service are used to show motion in real time of the teeth and jaws depicting six degrees of freedom. The computer receives anatomically correct 3D images of any portion of the craniomandibular system with a position sensor(s) attached. The position sensor data is then transferred with wireless attachments to the patient to generate true to life motion of the digital 3D models of the teeth and jaws.

In one embodiment, a computer or cloud based service is used to correlate 3D real motion visualizations to physiologic measurements. True to life motion of anatomically correct 3D digital models allows one to see individualized function of the jaws and teeth. The addition of measurable physiologic variables will give a comprehensive understanding of craniomandibular system health and improve treatment.

The purpose of this disclosure is to describe an affordable, easy to use and highly accurate system to animate actual images of an individual's teeth in function. These 3D visualizations may be referenced by imaging a wireless position sensor system bonded directly to the teeth or anchored in the jaw. The data may be correlated to MRI images, CT, radiographs, dynamic tracking of jaw movement, jaw joint ultrasound results to present the user with a complete understanding of all jaw function that includes fusion imaging and radiographic or other sources to render real-time, three-dimensional, multifaceted results, as well as an ability to create advanced anatomical models of a given subject. Diagnosis and treatment of craniomandibular problems will see immediate improvement.

Although, 3D visualization has been described utilizing many imaging sources, this disclosure makes no attempt to claim the creation of 3D images. However, the claimed subject matter is typically dependent on imaging sources to build the file to which the motion system disclosed is applied.

Sleep apnea has become recognized as one of the most vital health problems associated with dentistry. Over 2 million sleep studies are performed annually. The American Academy of Sleep Medicine recommends a mandibular advancement appliance as the treatment of choice for mild or moderate sleep apnea, yet when a sleep study is done, there is not a way to determine where the jaw is positioned during apneaic episodes. Knowledge of the jaw position and correlation to other physiologic measurements are critical to the successful treatment of sleep apnea.

The dental signs and symptoms of sleep apnea are comprehensively grouped as craniomandibular disorders (CMD). Diagnosis and treatment of jaw joint and bite dysfunctions, which are the core of CMD, are among the most difficult issues in dentistry. The jawbone exhibits the most complex movements in the body. Operating with six degrees of freedom, it is the only bilateral functioning bone with Temporomandibular Joints (TMJ) on each side. The teeth together, in occlusion, is the terminal endpoint of motion of the jaw. Studies have shown that in pathology, this position is associated with TMJ problems, malalignment/crowding, headaches, and sleep apnea, among many other issues. When considering the detrimental effects of sleep apnea it is clear mandibular positioning plays a key role in adverse cardiovascular outcomes including coronary heart disease, stroke, and atrial fibrillation.

Magnetic resonance imaging (MRI); computed tomography (CT); radiographs; sonography; jaw tracking; electromyogram (EMG); digital photography; and exact replica, mounted models of the teeth are the most common diagnostic tools of CMD. This information, usually gathered at different times and locations, is used to formulate a diagnosis and treatment, often resulting in a slow, difficult and expensive process.

Jaw tracking is achieved with a sensory array that tracks a magnet attached to the lower front teeth. The magnet movement is graphically depicted on-screen in real-time, and dysfunction in the joints can be deduced by analyzing the tracing. Moreover, the previously known techniques only give physicians a three-dimensional graphic of a single point tracing, a limitation that makes it difficult to fully evaluate and understand the technical problems to be addressed, especially given the jaw's six-dimensional pitch, roll and yaw.

EMG is also an important component to analyzing jaw function. A dysfunctional jaw position will result in an adaptive posture of the jaw muscles through the neuromuscular system. Often, the adaptive posture is pathologic causing excessive tension in the musculature. This can result in headaches. TMJ problems, facial pain and even ear problems. In the body's attempt to maintain homeostasis, an individual may also begin to grind the teeth to eliminate the interferences that prohibit the muscles from functioning with equal tension. EMG can be correlated to jaw position for increased diagnosis and treatment ability. Three-dimensional jaw tracking graphics combined with EMG is vital to providing objective data for diagnosis and treatment. Images of the TMJs are again necessary, of the exact evaluation position, to help assemble a mental six dimensional picture of the jaw and both TMJs function.

A recent survey of those familiar with the prior art identified important features in any future TMD diagnostic tool, highlighting cost, ability to see the joints (in stasis and in motion) together with the other related jaw parts, the ability to analyze both TMJs at once, ease of training, and compatibility with other methods of diagnoses and treatments.

Currently, 3-D graphic depictions (e.g., Cerec, iTero, Lava, True Definition) are essentially static. Thus, any treatment derived from these systems is based on a habitual, even pathologic bite with little or no consideration of associated physiologic parameters. There is, therefore, a long-felt but unmet need for methods and means of combining static three-dimensional graphic depictions with measurements obtained from EMG, Jaw Tracking, and Joint Vibration/Sonography.

Due to the evidence of the relationship between jaw position, sleep apnea and adverse cardiac outcomes, it is imperative that physiologic measurements such as pulse oximetry, heart rate, blood pressure and heart activity (EKG) are directly correlated with the position and function of the craniomanibular system.

The ability to objectively record and review data regarding the jaw position in habitual function or in a given treatment position is essential. Regarding polysomnography (sleep studies), there is not a system that can track the jaw in its habitual state and relate positional data to polysomnographic data. Polysomnography includes EKG, EEGX, blood oxygen, respiratory rate, blood pressure, body position, limb movement, and REM.

Furthermore, orthodontic systems like Invisalign and Clear Correct (clear aligners) move teeth where they appear straight but with no objective data regarding proper function. A craniomandibular position sensor system that is correlated to physiologic data is essential to proper diagnosis and treatment, to ensure patients are treated with optimal care.

Diagnostic modalities for CMD, sleep apnea, orthodontics and restorative dentistry, are fragmented. It is imperative that 3D imaging, CAD/CAM capabilities, motion tracking and physiologic measurements like those associated with polysomnography are brought together in a cohesive system to improve care for an array of dental related health issues.

U.S. Patent application 20120015316 by Sachdeva, et al. describes the use of jaw tracking with every visualization method known to man to acquire 3D models. Jaw tracking methods available at the time of the aforementioned application have been in use for decades. There is no reference to correlating physiologic parameters including EMG, joint sonography (recording and analyzing joint sounds), EKG, pulse oximetry, blood pressure, heart rate, pharyngometry or rhinometry. There is a vague reference to telemetric jaw tracking, but there is no description of how such device works.

U.S. Pat. No. 5,826,579 to Remmers, et al. is Somnomed's positioner, MATRx. It moves the jaw anterior and posterior, with the teeth locked in trays. It gives data relating the jaws A/P position to physiologic measurements, but it is a manipulated position. It cannot give functional data without a large controller in the mouth. Furthermore, there is no way to relate the physiologic data to 3D anatomic models in the natural functioning jaw positions of a patient.

Another interesting disclosure is U.S. Pat. No. 7,402,996 to Arai et al. which uses a minimum of 5 magnets each attached to a wire and a magnetism generator. The subject to be tracked with this device must then be placed inside of a magnetic field sensor. It is a highly accurate device, but it is not wireless nor does it correlate to 3D imaging.

U.S. Pat. No. 8,667,972 to Makkar et al. discloses the fabrication of a mouthpiece from a bite registration acquired using jaw tracking and EMG analysis. Makkar, et al. discuss the use of impressions and molds of the teeth and does not describe the correlation to digital data or a functional analysis. Furthermore, Makkar does not reference MyoTronics U.S. Pat. No. 4,765,345 to Adib regarding jaw tracking, or U.S. Pat. No. 4,344,441 to Radke regarding electromyography of the mandibular musculature. Adib's disclosure regarding jaw tracking is a sensory array Velcro strapped to the head that tracks a magnet placed on the lower teeth with sticky wax. Visualization of data is displayed as a frontal and sagittal graph of the motion. It does not correlate to a 3D image of the teeth or jaws. Radke's patent describes an electromyographic system to measure function of the jaw muscles. Both of the aforementioned patents assigned to Myo-Tronics are for the K7 evaluation system which correlates EMG of the muscles with tracking of the jaw position, but not to a graphic visualization of an individual's teeth or jaws.

Other closely related disclosures, U.S. Pat. Nos. 8,226,407 and 8,550,816 to Hanewinkel, et al. discuss the association of pharyngometer results with a manual or robotic device that protrudes outside of the mouth for the manipulation of the jaw and recording the bite position with registration material. It is not a system that can gather data on position in everyday function, nor does it give data that can demonstrate normal functional movements and is useless during polysomnography. U.S. Pat. No. 8,620,045 to Adams is a video camera based tracking system with fiduciary makers. It is not a wireless positioning sensor system as RFID, bluetooth or data storage are not referenced. Adams mentions measuring muscle function, but makes no reference to the method of acquiring such data.

U.S. Pat. No. 5,989,023 to Summer, et al. is a wireless motion system that records the projection of light from a source mounted adjacent to a dental arch. It too is a novel system but like the above listed disclosures, none define relating jaw position to a panel of physiologic measurements, in particular EMG, EKG, EEG, pulse oximetry, blood pressure, heart rate, respiratory rate, tooth contact sensors, pharyngometry or rhinometry.

In one embodiment, a computer or cloud based service is used to correlate 3D real motion visualizations to physiologic measurements. True to life motion of anatomically correct models allows one to see individualized function of the jaws and teeth. CAD/CAM Software is used to design one or more appliances to move the teeth to a new bite position. Appliances are milled, or 3D printed to physiologic measurements such as electromyography, pulse oximetry, blood pressure, heart rate, respiratory rate, pharyngometry, rhinometry, tooth contact sensors, cervical and vertebral posture, among others.

In one embodiment, digital anatomical models are used to design appliances whether for palliative orthopedic repositioning, dental reconstruction, orthodontic aligners, space maintainers or sleep apnea appliances that could be printed, milled or sent to a lab for fabrication. This disclosure integrates anatomical models and physiologic measurements of a given individual to produce a treatment result that includes specific inter-occlusal dimensional changes.

Current methods of treating malocclusions with orthodontic aligners, sleep apnea with mandibular advancement appliances, and bruxism or TMJ dysfunction with removable appliances use either manual polyvinyl impressions and stone models, or 3D imaging and printing of models. Each of the aforementioned health problems are related in that they are all craniomandibular disorders, (CMD)

Sleep apnea has become recognized as one of the most vital health problems to be addressed by dentists. The dental signs and symptoms of sleep apnea match those more comprehensively known as CMD. One of the biggest hurdles in dentistry is in the diagnosis and treatment of jaw joint and bite dysfunctions which are the core of CMD. The jawbone exhibits the most complex movements in the body. Operating with six degrees of freedom, it is the only bilateral functioning bone with Temporomandibular Joints (TMJ) on each side. The teeth together in occlusion are the terminal endpoint of motion of the jaw. Studies have shown that this position when pathologic is associated with TMJ problems, mal-alignment/crowding, headaches, and sleep apnea, among many other issues. When considering the detrimental effects of sleep apnea systemically, it is clear that given the correct diagnosis, mandibular positioning plays a role in adverse cardiovascular outcomes including coronary heart disease, stroke, and atrial fibrillation.

Over 2 million sleep studies are performed annually. The American Academy of Sleep Medicine recommends a mandibular advancement appliance as the treatment of choice for mild or moderate sleep apnea, yet when a sleep study is done, there is not a way to determine where the jaw is positioned during apneaic episodes. Knowledge of the jaw position and correlation to other physiologic measurements are critical to the successful treatment of sleep apnea.

Invisalign is a system to straighten teeth with clear aligners; however, there are no associations to physiologic data. This is imperative knowledge considering the affiliations to systemic conditions that malocclusions are related to.

Current diagnostic modalities for jaw dysfunctions include magnetic resonance imaging (MRI); computed tomography (CT); radiographs; sonography; jaw tracking; electromyography (EMG); digital photography; and exact replica, mounted models of the teeth. This information, usually gathered at different times and locations, is used to formulate a diagnosis and treatment, often resulting in a slow, difficult and expensive process.

Jaw tracking is achieved with a sensory array that tracks a magnet attached to the lower front teeth. The magnet movement is graphically depicted on-screen in real-time, and dysfunction in the joints can be deduced by analyzing the tracing. Moreover, the previously known techniques only give physicians a three-dimensional graphic of a single point tracing, a limitation that makes it difficult to fully evaluate and understand the technical problems to be addressed, especially given the jaw's six-dimensional pitch, roll and yaw.

EMG is also an important component to analyzing jaw function. A dysfunctional jaw position will result in an adaptive posture of the jaw muscles through the neuromuscular system. Often, the adaptive posture is pathologic causing excessive tension in the musculature. This can result in headaches, TMJ problems, facial pain and even ear problems. In the body's attempt to maintain homeostasis, an individual may also begin to grind the teeth to eliminate the interferences that prohibit the muscles from functioning with equal tension. EMG can be correlated to jaw position for increased diagnosis and treatment ability. Three-dimensional jaw tracking graphics combined with EMG is vital to providing objective data for diagnosis and treatment. Images of the TMJs are again necessary, of the exact evaluation position, to help assemble a mental six dimensional picture of the jaw and both TMJs function.

Current 3-D graphic systems (e.g., iTero, Lava, True Definition) are static. Thus, any treatment derived from these systems is based on a habitual, even pathologic bite with little or no consideration of associated physiologic parameters. There is, therefore, a long-felt but unmet need for methods and means of combining static three-dimensional graphic depictions with measurements obtained from EMG, Jaw Tracking, and Joint Vibration/Sonography.

The relationship between jaw position, sleep apnea and adverse cardiac outcomes, dictates that it is imperative that physiologic measurements such as pulse oximetry, heart rate, blood pressure and heart activity (EKG) are directly correlated with the position and function of the craniomanibular system to optimize diagnosis and treatment.

The time has come to disclose a system that fosters the creation of dental treatment appliances that are fabricated to objective physiologic data, whether it is removable or bonded, for bruxism, sleep apnea or orthodontics, milled, 3D printed, or lab fabricated and from any material that can be produced by these methods.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION OF THE FIGURES

Figure 1:
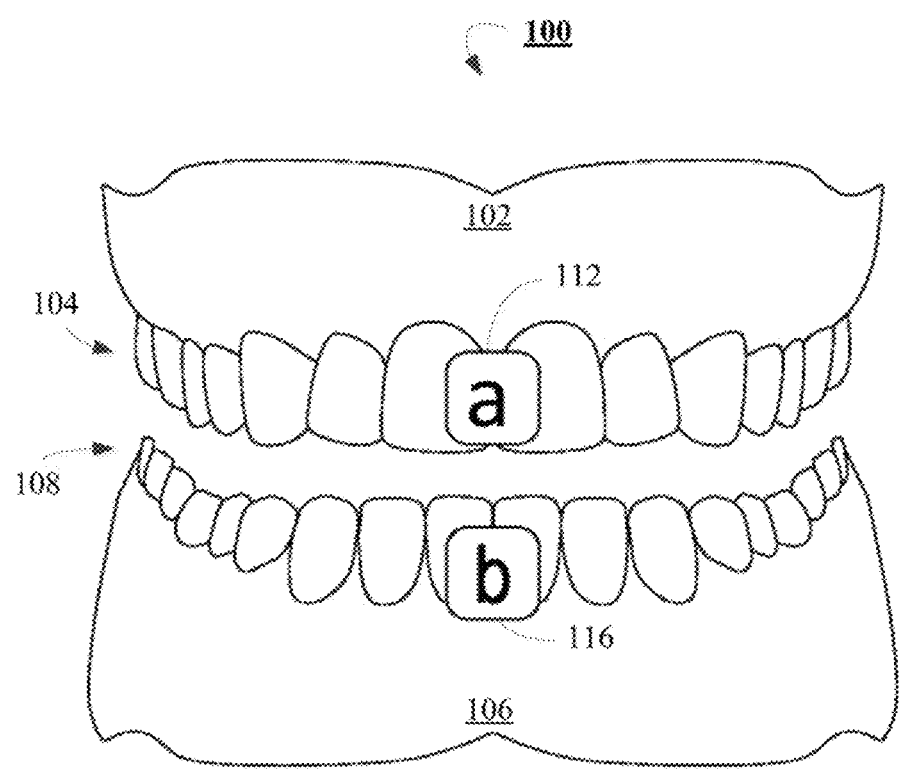
FIG. 1 is an illustration of jaws and teeth with sensors attached in accordance with the claimed subject matter.

In the context of this document, a "memory" or "recording medium" can be any means that contains, stores, communicates, propagates, or transports the program and/or data for use by or in conjunction with an instruction execution system, apparatus or device. Memory and recording medium can be, but are not limited to, an electronic, magnetic, optical, electromagnetic or semiconductor system, apparatus or device. Memory and recording medium also includes, but is not limited to, for example the following: a portable computer diskette, a random access memory (RAM), a read-only memory (ROM), an erasable programmable read-only memory (EPROM or flash memory), and a portable compact disk read-only memory or another suitable medium upon which a program and/or data may be stored.

As the Inventor herein has realized, existing technology is limited. For example, the MRI test is considered the gold standard, providing information on the integrity of both the hard and soft tissues, whereas CT scans only visualize hard tissue. These modalities offer detailed images of the jaw joints, but give no insight as to function. Furthermore, since the images are taken in a supine position (lying down), an inaccurate depiction of the true position of the jaw is obtained as it falls back with gravitational forces.

A recent survey of those familiar with the prior art identified important features in any future TMD diagnostic tool, highlighting cost, ability to sec the joints (in stasis and in motion) together with the other related jaw parts, the ability to analyze both TMJs at once, ease of training, and compatibility with other methods of diagnoses and treatments.

Currently, 3-D graphic depictions (e.g., Cerec, iTero, Lava, True Definition) are essentially static. Thus, any treatment derived from these systems is based on a habitual, even pathologic bite with little or no consideration of associated physiologic parameters. There is, therefore, a long-felt but unmet need for methods and means of combining static three-dimensional graphic depictions with measurements obtained from EMG, Jaw Tracking, and Joint Vibration/Sonography so that clear aligners can thereafter be designed and printed in any dental office. Other physiologic measurements include pulse oximetry and heart activity.

In one embodiment, a plurality of radio transceiver micro controllers with magnetometers are placed on one arch and a magnet(s) on the opposing arch, which may also be used with accelerometers and/or gyrometers. A 3D scanner, 3D CBCT or other system capable of generating 3D files will be used to create 3 pairs of files (with and without sensors) of the teeth and jaws. The three pairs are the upper teeth, the lower teeth and of the teeth together at the habitual bite in a clench. The pairs are correlated to display with and without tracking sensors attached to the teeth. The teeth together in habitual bite are the zero point. Tracking sensor data may also be applied to the 3D images without images of the sensors in place. Synchronization via time stamping allows for correlation of tracking data to other physiologic data inputs after downloading when wireless connectivity cannot be established.

The position for the digital 3D models begins with setting the HIP plane of the maxilla level to the horizon. The right and left Hamular notches and incisive canal are selected on the digital models, whether on photograph, video, radiography (CT). The horizontal plane of these three points can be compared to a photograph of the patient standing upright to determine the correct plane and smile line in relation to the HIP selection. The motion capture data is then applied to the 3D models to show function and range of motion of the jaw. At any point in recording of data, multiple freeze frame positions of the spatial relationship between the upper and the lower jaw can be saved. Measurement tools precisely determine the spatial dimensions at freeze frame positions between pairs of upper and lower teeth to determine pitch, roll, yaw, lateral shift of the jaw.

In some treatment methods, as with Transcutaneous Electric Neural Stimulation, there is a significant change in the mandibular posture in relation to the cranium and upper teeth. This disclosure includes calculating the exact square area and dimensions of the teeth to gain full contact of the teeth based on a treatment trajectory. A treatment choice may be determined to either reshape the teeth mechanically, or move the teeth to a new bite position. Correct determination is critical as excessive removal of tooth structure can be destructive and orthodontics could be unnecessary to correct a bite.

Transcutaneous Electric Neural Stimulation, anterior deprogramming and centric relation are among the many methods used to treat TMJ issues, malocclusion, sleep apnea and a myriad of functional dental problems. Each one is capable of changing the bite. This disclosure provides a method to measure the difference between habitual bite and a new treatment position.

It is imperative to determine how much tooth structure has been worn down, but first, the physiologic position of rest for the lower jaw must be found, then the trajectory of jaw movement and initial contact position of the teeth sought before calculating the need for adding or taking away tooth structure. Wear facets on each tooth are analyzed to determine the exact area of missing tooth structure after correlating positional data to photography, 3D video, 3D CT or digital radiography.

It is known that excessive tooth structure removal is considered destructive. Occlusal equilibration-dentists grinding the teeth with diamond burs to get a better bite is performed regularly with no calculations on tooth structure that has already been damaged and worn away by one's own bite forces and grinding of the teeth. This disclosures algorithms provide precise calculations of how much tooth structure is missing and how much more would be necessary to remove on each individual tooth to achieve a particular final bite position. If the area for removal appears to be destructive after inclusion of the worn away dentition, then calculations are made to determine how much tooth structure must be added to each tooth to achieve a stable physiologic bite. These additions may alter the bite by changing the vertical, anterior-posterior, lateral shift, pitch, roll and yaw of the relationship between the maxillary and mandibular teeth. Therefore, measurements of the space between the maxillary and mandibular teeth are made at several positions to determine the displacement vector and position vector. Vector forces are also determined by algorithms calculated from mandibular motion tracking.

If it is determined that equilibration can be done, then based on the physiologic trajectory, precise areas to be adjusted are shown graphically for each tooth on the digital 3D models. Adjustment coping trays may also be created by milling or 3D printing so that only the exposed areas of the tray are open to indicate areas to be adjusted. If equilibration is not indicated, then an appropriate physiologic bite position can be chosen. In this scenario, the teeth may be completely apart, or at the first contact of a single pair of upper and lower teeth where the remaining teeth are apart.

As a modular system, a user may add other data sources such as simultaneous ultrasound imaging of the jaw joints as correlated to radiographs, CT or MRI to give positional data with six degrees of freedom. Matching reference points are selected between the ultrasound images and CT/MRI images to be synchronized so that a fully functional digital model may be displayed. If only unilateral ultrasound images are available, then the positional sensors described above in the primary embodiment can be utilized upon 3D visualization to display a dynamic functional model. In either scenario, the measurements described in the primary embodiment are applicable. A dual ultrasound probe correlated with 3D CT also works as a standalone solution or with wireless position sensors to animate mandibular motion. The use of both would allow for duplicity and verification of accuracy between the animated motion solutions.

The system contemplated herein, then, comprises one or more wireless sensory devices used to capture motion data. This data correlated with digital 3D models provides valuable information regarding jaw function and motion to dentists, orthodontists, and oral surgeons.

The functional digital models have the ability to combine with other imaging systems to present the user with a complete graphic analysis of what is occurring in the jaw joints and the relationship between the upper and lower teeth. The correlated data points are used to create an accurate functional anatomic graphic of the craniomandibular complex in real time or via timestamp.

The sensor data and visualization can be combined with three-dimensional CTs, MRIs and ultrasound, which will allow mandibular tracking, animate fusion of anatomic models, three-dimensional imagery, and a meaningful correlation of joint sounds within the digital model. Jaw position sensor data is also correlated with Pulse Oximetry, heart rate, ECG of the heart, brain EEG, REM, Blood pressure, and skeletal muscle EMG in real time, either simultaneously or with time stamping. EMG activity of the jaw muscles, including wireless EMG data that can be customized to a graphical display and show tissue simulation of function for the muscle groups of the jaw, whereby the muscles change color for various EMG levels between rest and extreme hyperactivity. Muscle tissue may also be visualized with ultrasound and depict pathology such a taut bands of muscle fibers on the comprehensive display, such that all the craniomandibular muscles may be displayed on the anatomic model.

The craniomandibular position sensor data is also be compatible with a manual or electronic jaw positioner. Electronic jaw positioners are currently used during sleep studies to adjust anterior and posterior movements. This data could then be transferred to the digital 3D models to display the exact position of the craniomandibular complex.

Another addition is the correlation of pharyngometry, rhinometry or other airway measurements that give data regarding dimensions of the airway. This is critical data in understanding the relationship of the jaw position and available airway space.

Cervical and other postural vertebral data is another important correlate. The center of rotation for the mandible is between C1-C2. Studies have shown that malalignment of the craniomandibular complex affects vertebral posture and vice versa. Real-time analysis showing the relationship between craniomandibular and vertebral posture is therefore integral to connecting supportive healthcare providers such as chiropractors, physical therapists and medical doctors.

Position sensor data as related to 3D imaging shows the contact position of the teeth as the beginning point of motion. Those contacts are confirmed by correlation with tooth contact sensor data. Foil thin bite wafers are placed between the teeth that display the amount of pressure on any given tooth contact. Correlation of these two data sources serves as verification and increased accuracy of the dynamic 3D models.

In a particular, non-limiting embodiment, one or more wireless sensors using accelerometers, magnetometers and gyroscopes are bonded to the teeth or affixed to the jaw. Image capture with any 3D visualization (video, MRI, CT, radiographs, ultrasound) system to create 3D graphical models is then put into motion based on the data from the tracking sensors. The sensor data may be transmitted via Bluetooth, radio frequency or any wireless transmission method. The 3D visualizations will show jaw position in relation to heart activity (EKG), pulse oximetry, EMG of jaw muscles as well as correlation to cervical spine and other postural measurements that will affect jaw positioning.

In another non-limiting embodiment, the device utilizes high frequency ultrasound probes (e.g., 12-15 MHz) to see a maximum visible depth of 10-15 millimeters and allow detailed measurements of the joint and disc location. Various companies already exist which currently produce probes that can be used for this purpose. In one specific embodiment, the area to be visualized is approximately 15 millimeters by 40 millimeters.

An adjustable mounting system places the probes in an appropriate position for scans. In an alternative embodiment, the hardware is a stand-alone system, outfitted such that it can move freely from patient to patient as necessary. In another embodiment, the hardware is securely attached to a dental chair or other area used for stationary diagnostics.

Software development enables visualization of both TMJs in an easy-to-interpret digital format, which allows for more accurate diagnoses, more effective treatment options, and comparisons of teeth in a current position to teeth in an ideal position. The data visualized is combined with one or more of audio sonography, jaw tracking, EMG analysis, layered with three-dimensional cone beam CT images, 3D digital images of the teeth and correlated with the previously discussed physiologic measurements for a complete analytic system.

In one embodiment, the software has the capacity to custom design inter-occlusal appliances or orthodontic aligners that may be produced with a 3D printer, milled, or fabricated in a lab.

Bruxism/Athletic Performance

Orthotics, orthopedic repositioning appliances, night guards and protective or performance appliances may be produced in various ergonomic arrangements. In a preferred embodiment, a bite position is chosen to treat in and an appliance design is chosen from a library. The appliance detail is formed on the shape of an individual's teeth and customized based on motion analysis and an optimal treatment position according to physiologic measurements. Treatment of dysfunctions are readily achieved with a series of three-dimensionally printed orthodontic, orthopedic repositioning appliances and/or jaw aligners designed in correlation with one or more physiologic measurements such as Pulse Oximetry, heart activity, respiratory rate, EMG, EEG, EKG, joint sonography, jaw tracking-magnetic, video, ultrasound, radio transmitter and any other as yet undeveloped but compatible systems.

Sleep Apnea

In still further embodiments, appliances milled, printed or otherwise produced in accord with physiologic measurements comprise sleep apnea appliances. Digital 3D models of the teeth are acquired and a treatment position is chosen within the parameters and correlation of physiologic measurements with or without motion analysis. A particular appliance design is selected from a library of sleep apnea appliance designs and applied to the physiologic inter-occlusal model space. Customization tools in the software allow the technician to create an individualized appliance in accordance with objective physiologic data measurements. A doctor may utilize 3D printing or milling to deliver these appliances in a much more efficient manner than is currently available.

Orthodontics

In another specific though non-limiting embodiment, aligners may comprise incremental steps in changing the positioning of the teeth in accord to a predefined, specific inter-occlusal spatial dimension. Currently known aligners (such as Invisalign, Clear Correct, etc.) cannot correct vertical, pitch, roll or yaw changes to the bite and are not correlated to other associated physiologic data as mentioned above.

The system may employ brackets, rubber bands, and/or buttons and wells on aligners to achieve a desired eruption position for the teeth. The foregoing detailed description is intended primarily for illustrative purposes, and is not intended to include all possible aspects of the present invention. Moreover, while the invention has been shown and described with respect to an exemplary embodiment, those of skill in the pertinent arts should appreciate that the foregoing detailed description, and various other modifications, omissions and additions, so long as the general form and detail thereof, may be made without departing from either the spirit or scope of the present invention.

Fremitus, tooth mobility, wear facets or advanced attrition and many other conditions as correlated to functional and physiologic measurements have gone poorly analyzed due to lack of development of high-tech tools. Fremitus on orthodontically treated anterior teeth is commonly seen everyday clinically, yet there are no studies that discuss mobility of front teeth after orthodontics. A pubmed search for "fremitus and orthodontics" resulted in 3 studies that vaguely discuss mobility of the anterior teeth. There were no studies when searching "premature contact and tooth morbidity". A tooth that has been left in traumatic (hyper) occlusion without proper adjustments (overfilled filling or crown hitting first) usually develops mobility, yet only 3 studies returned on pubmed when searching "premature contact and tooth mobility". Of those, only one was relevant and indicated that jaw movements which deviated from normal chewing movements increased the mobility of specific types of teeth. [23] This disclosure is a visualization system that correlates motion and functional analysis with physiologic data will give dentists the ability to easily analyze these conditions.

Reconstructive Crowns, Bridges, Implants, Prosthetics

In another example, images may be acquired with video from a system such as CEREC, Itero or 3M's True Definition Scanner. These images are currently converted to static 3-D models. The software described herein combines the static 3-D models with data acquired from EMG, Jaw Tracking, Joint Vibration/Sonography or any of the other above mentioned medical imaging applications to render a true physiologic anatomic model of the human craniomandibular complex. Once a new treatment position is determined an appliance or dental prosthesis is designed and printed, milled or sent to a lab for fabrication to begin treatment.

In each embodiment, treatment is centered on physiologic data. In reconstructions, Golden proportions, a ratio of 1.618:1, ideal curvatures (Spec & Wilson) in the sphere of occlusion, horizontal smile line and other components of posture are capable of optimization within the scope of this disclosure.

The treatment scenarios and aforementioned embodiments may also be correlated to sonography (joint sounds or vibration), or ultrasound imaging in a comprehensive evaluation system. They may also correlate to physiologic data from (but are not limited to) pharyngometer, rhinometer and any other appropriate airway measurement.

Turning now to the Figures, FIG. 1 is an illustration of jaws and teeth, or teeth/jaw system 100, with sensors attached in accordance with the claimed subject matter. An upper jaw 102 includes teeth 104 and a lower jaw 106 includes teeth 108. An A sensor 112 is attached to the middle teeth of teeth 104 and a B sensor 116 is attached to the middle teeth of teeth 108

In one embodiment, teeth 104 and 108 are prepared for bonding. A delivery jig (not shown), affixed to both sensors 112 and 116 of the sensor pair (A & B) ensure that the pair 112 and 116 are in a calibrated position. In an alternative embodiment, the sensor pair 112 and 116 are calibrated after installation on teeth 104 and 108. The sensor pair 112 and 116 is positioned and bonded with teeth 104 and 108 closed together such that an upper tooth and lower tooth have a bonded component, then the delivery jig is removed with the pair of sensors 112 and 116 are in calibration and normal function can be measured. After data collection is complete, sensor pairs 112 and 116 are removed and the residue of the bonding material is removed from teeth 104 and 108.

In one embodiment, sensor pair 112 and 116 are positioned on opposing teeth 104 and 108, respectively, at the back of the jaws 102 and 106, respectively, to minimize the potential distance between sensors 112 and 116 when teeth 104 and 108 are apart. Multiple sensor pairs (not shown) may also be employed.

Figure 2:
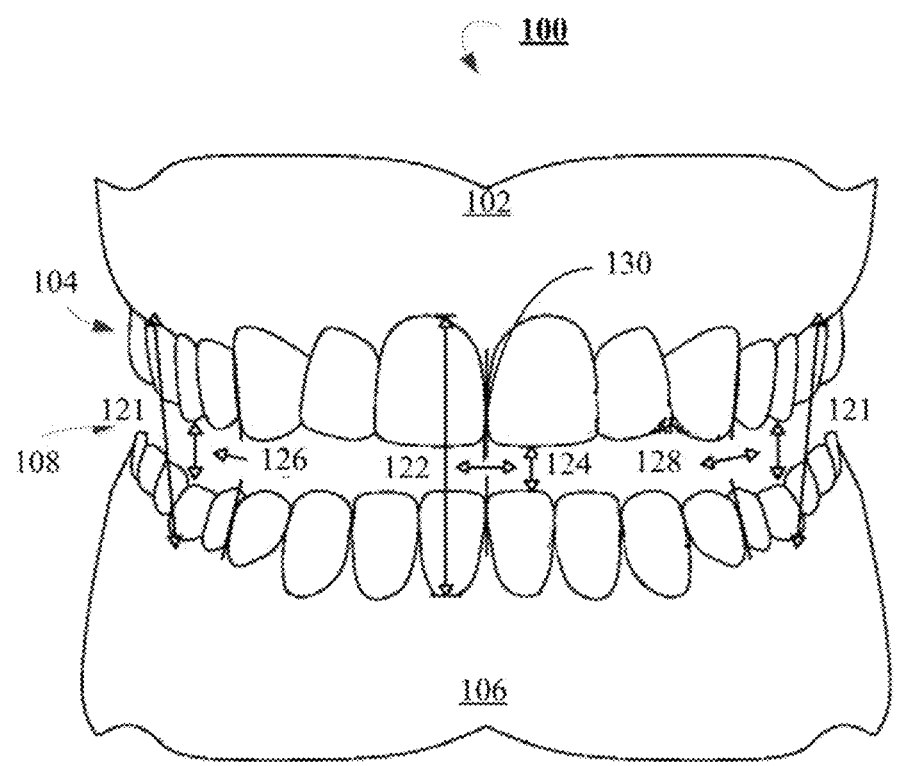
FIG. 2 is an illustration of the teeth and jaws of FIG. 1 showing dimensional relationships as measured between the upper and lower teeth/jaws in a clench to compare to treatment positions.

FIG. 2 is an illustration of teeth/jaw system 100, including upper and lower jaws 102 and 106 and teeth 104 and 108 of FIG. 1, showing dimensional relationships as measured between upper and lower jaws 102 and 106 and teeth 104 and 108 in a clench to compare to treatment positions.

Lower jaw 108 moves with six (6) degrees of freedom. The following measurements may be taken to accurately define the spatial relationship of lower teeth 108 to upper teeth 104.
 a) CEJ-CEJ 121 on a posterior pair 121 of teeth 104 and 108 on the right and left in the closed bite.
 b) CEJ-CEJ 122 on a pair of anterior teeth in the closed bite.
 c) Inter-occlusal space 124 is the difference between a & b above, when compared to various positions.
 d) Anterior-Posterior shift 126 of jaw 102 on the right.
 e) Anterior-Posterior shift 128 of jaw 102 on the left.
 f) Midline/lateral shift 130.
Briefly, the spatial relationships a-f can be compared to show changes in the x, y, z axes with respect to pitch, roll and yaw.

Figure 3:
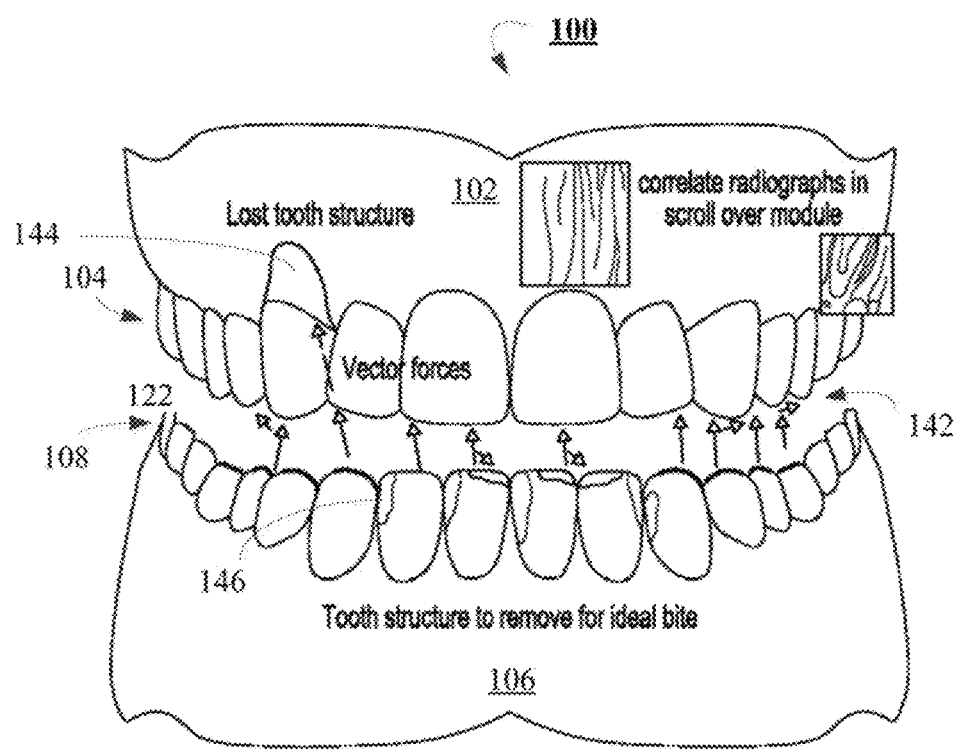
FIG. 3 illustrates a functional analysis of the teeth/jaw system of FIGS. 1 and 2.

FIG. 3 illustrates a functional analysis of teeth jaw system 100, including upper and lower jaws 102 and 106 and teeth 104 and 108, introduced above in conjunction with FIGS. 1 and 2. This graphic representation demonstrates damage to the teeth caused by vector forces 142 measured with sensor tracking in accordance with the claimed subject matter. Wear patterns on the teeth, recession and abfraction of the gum/ root area of the teeth are indicated in an area 144.

Additionally, tooth structure 146 that may be necessary to be removed in accordance with the claimed subject matter to idealize how the teeth come together is displayed. Radiographs and 3D video/photo images are used to calculate the surface area of the tooth that a patient has worn away by grinding the teeth together to determine how much wear has already occurred.

Figure 4:
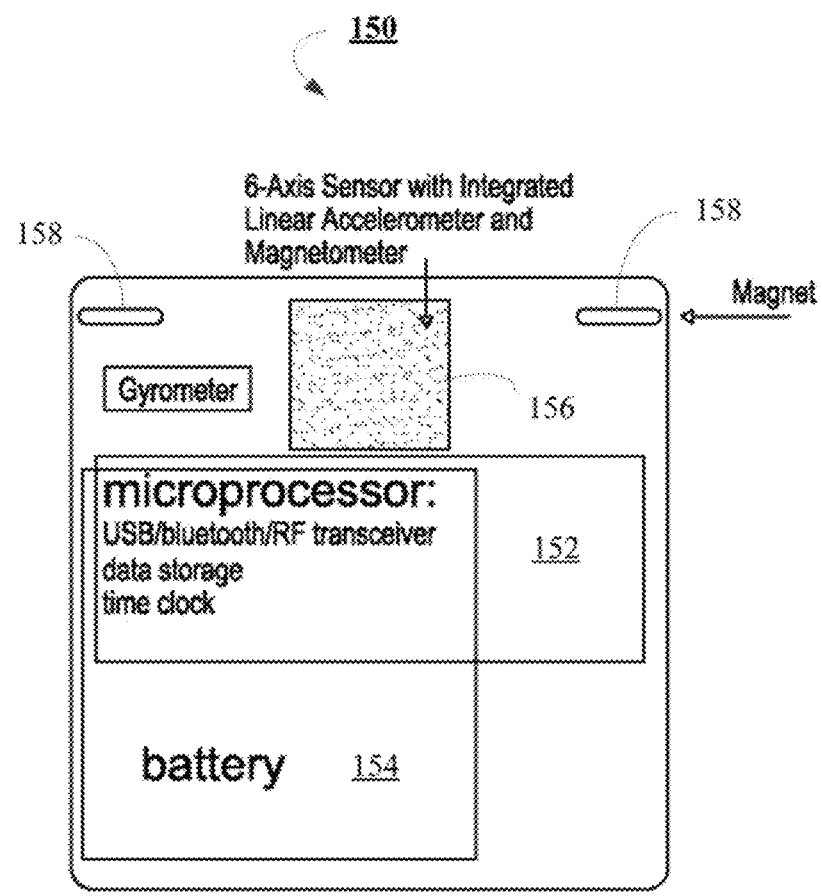
FIG. 4 is an illustration of a layout one embodiment of a sensor in accordance with the claimed subject matter.

FIG. 4 illustrates a layout of a sensor 150 that may implement the claimed subject matter. In one embodiment, a pair of sensors (sec 112, 116, FIG. 1) with a microprocessor, data storage, time clock, battery 154 and magnetometer 156 are placed on lower jaw 106, while a pair of magnets 158 are placed on the opposing jaw 102. Additional embodiments, may include an accelerometer, gyroscope, compass, bluetooth and RF transceiver in sensor 156. In the alternative, only one sensor and one magnet may be used. It should be noted that, if place at the rear of jaw, the potential distance between the sensor and the magnet is minimized for potentially more accurate measurements. It should be noted that FIG. 4 illustrates only one potential sensor configuration. The placement of magnets, accelerometers and so on may be on one or both of a pair in different numbers.

Figure 5:
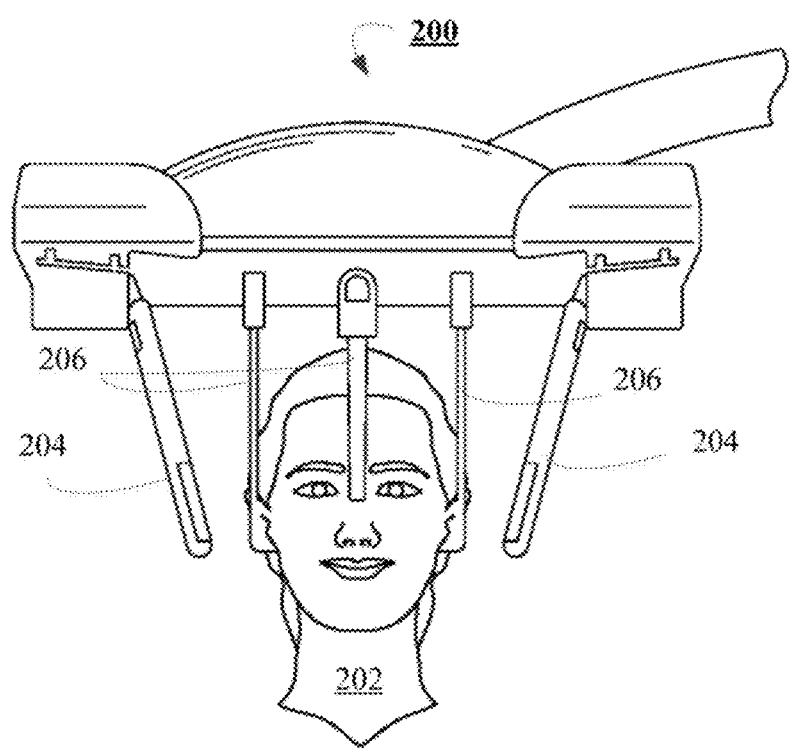
FIG. 5 is an illustration of a patient undergoing a simultaneous bilateral ultrasound.

FIG. 5 is an illustration 200 of a patient 202 undergoing a simultaneous bilateral ultrasound. Such ultrasound Imaging of right and left TMJ's gives positional information regarding the joint disc and motion tracking by tracking marked data points and correlating to position sensor motion tracking. Included are a pair of ultrasound transmitter/ receivers 204 and arms 206 to hold the patient's head in position during measurements.

Figure 6:
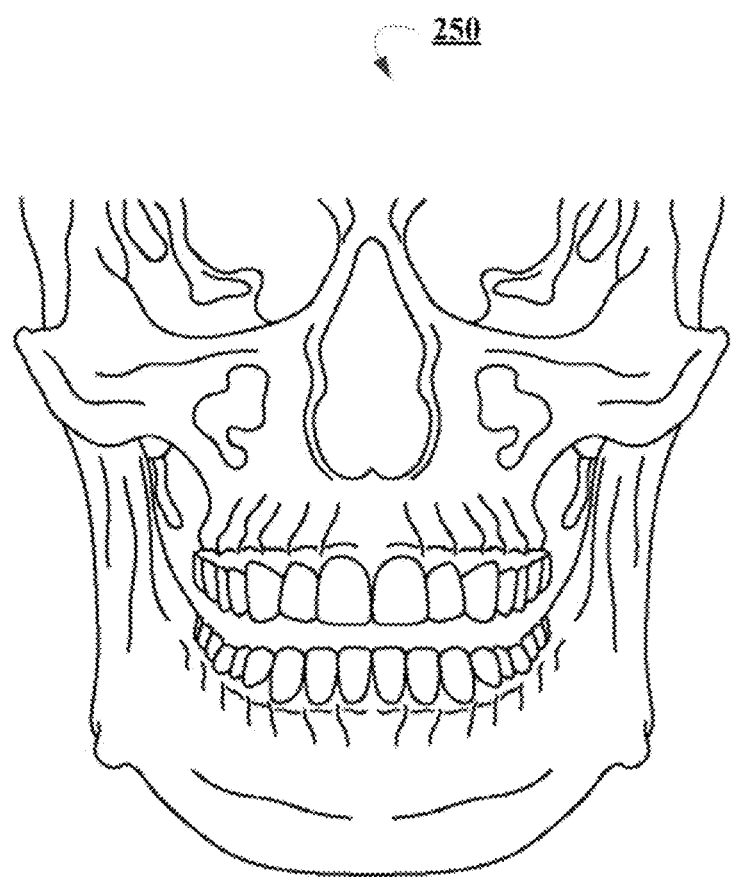
FIG. 6 is an illustration of a 3-dimension (3D) computerized axial tomography (CT) scan.

FIG. 6 is an illustration of a 3-dimension (3D) computerized axial tomography (CT) scan 250. Scan 250 represents acquisition of bony anatomy for 3D volume to be correlated with other data, as explained in more detail below in conjunction with FIGS. 7-10.

Figure 7:
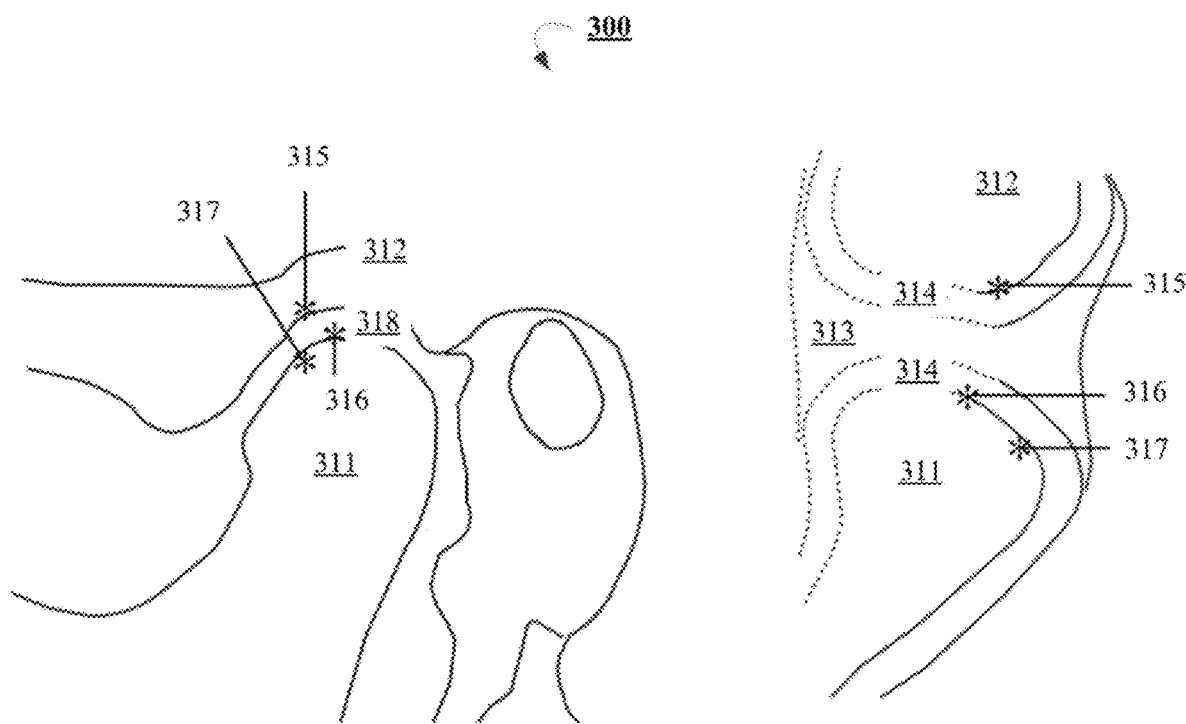
FIG. 7 illustrates two (2) of a temporomandibular joint (TMJ), including a Sagittal CT view and a view of a Coronal ultrasound section.

FIG. 7 illustrates two (2) of a temporomandibular joint (TMJ), including a Sagittal CT view 302 and a view of a Coronal ultrasound section 304. Numbered elements and data points in views 302 and 304 correlate with each other. Elements shown in each view 302 and 304 include a mandibular condyle 311, a temporal bone 312, an articular disk 313 and a joint capsule 314. Correlated data points, which include data points 315, 316 and 317, provide positioning information so that a space 318 in 3D CT 302 may be fused with ultrasound data 304, positioning sensor 156 (FIG. 4) and other accessory data.

A plurality of data points are selected to correlate between the 3D CT and ultrasound so that soft tissue data in the ultrasound (see FIG. 5) is fused with the 3D CT (see FIG. 6). Motion of the fused system based on ultrasound is correlated with position sensor motion tracking for rendundacy checks. Data points include mandibular condyle 311, temporal bone 312, articular disc 313 and joint capsule 314. Points that may be correlated between the 3D CT scan and the ultrasound include points 315, 316 and 317. In addition, soft tissues joint space 108 may be visualized in an ultrasound.

Figure 8:
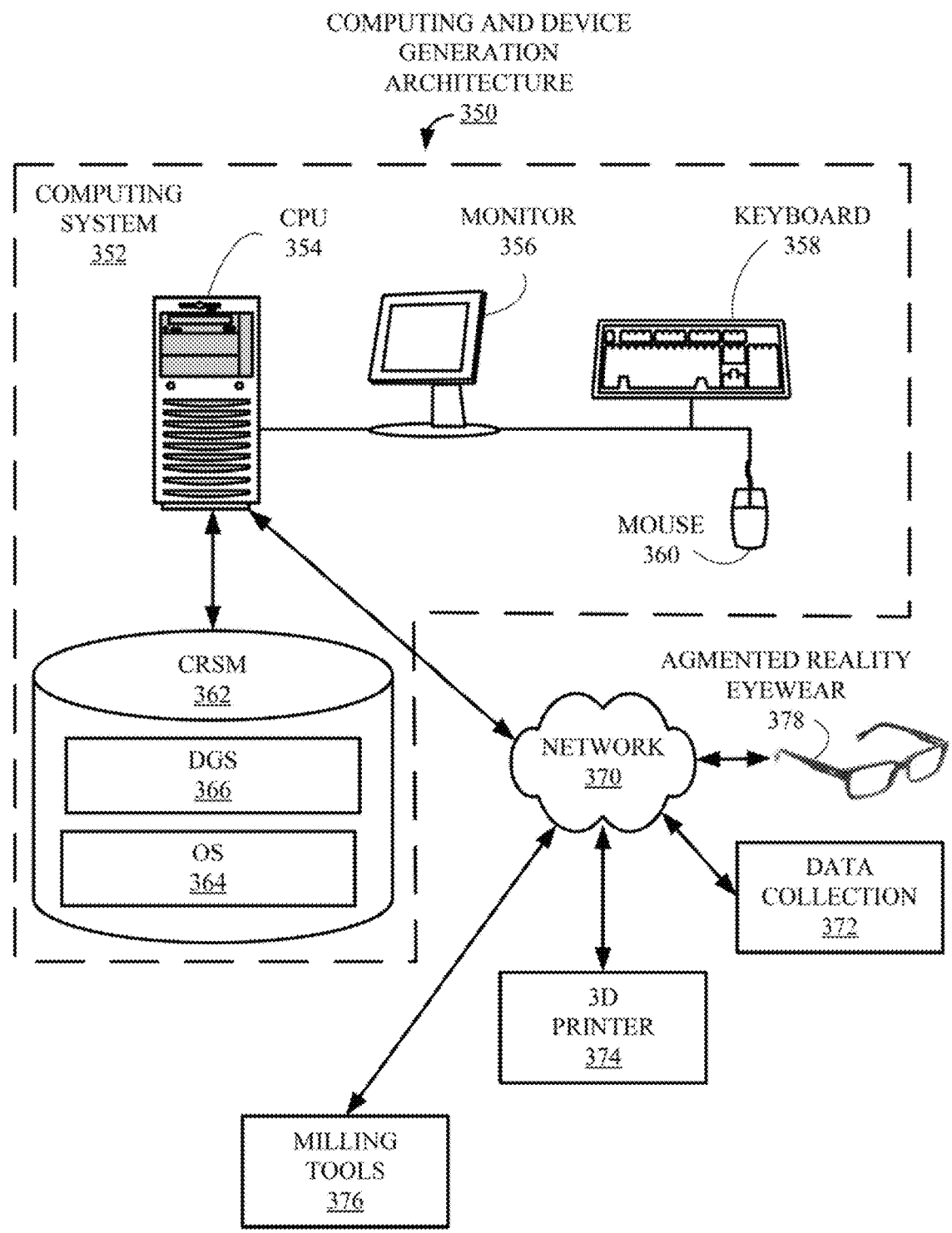
FIG. 8 is a block diagram of a computing architecture in which the disclosed technology may be implemented

FIG. 8 is a block diagram of a computing and device generation architecture 350 in which the disclosed technology may be implemented. A computing system 352 includes a central processing unit (CPU) 354, coupled to a monitor 356, a keyboard 358 and a pointing device, or "mouse," 360, which together facilitate human interaction with computing system 350 and computing system 352. Also included in computing system 352 and attached to CPU 354 is a computer-readable storage medium (CRSM) 362, which may either be incorporated into computing system 352 i.e. an internal device, or attached externally to CPU 354 by means of various, commonly available connection devices such as but not limited to, a universal serial bus (USB) port (not shown). CRSM 362 is illustrated storing an operating system (OS) 364 and an example of computing code, or device generation system (DGS), 366 that, in the following examples implements aspects the claimed subject matter. It should be noted that a typical computing system would include more than one application, but for the sake of simplicity only one is shown. DGS 366 is described in more detail below in conjunction with FIGS. 9-10.

Figure 9:
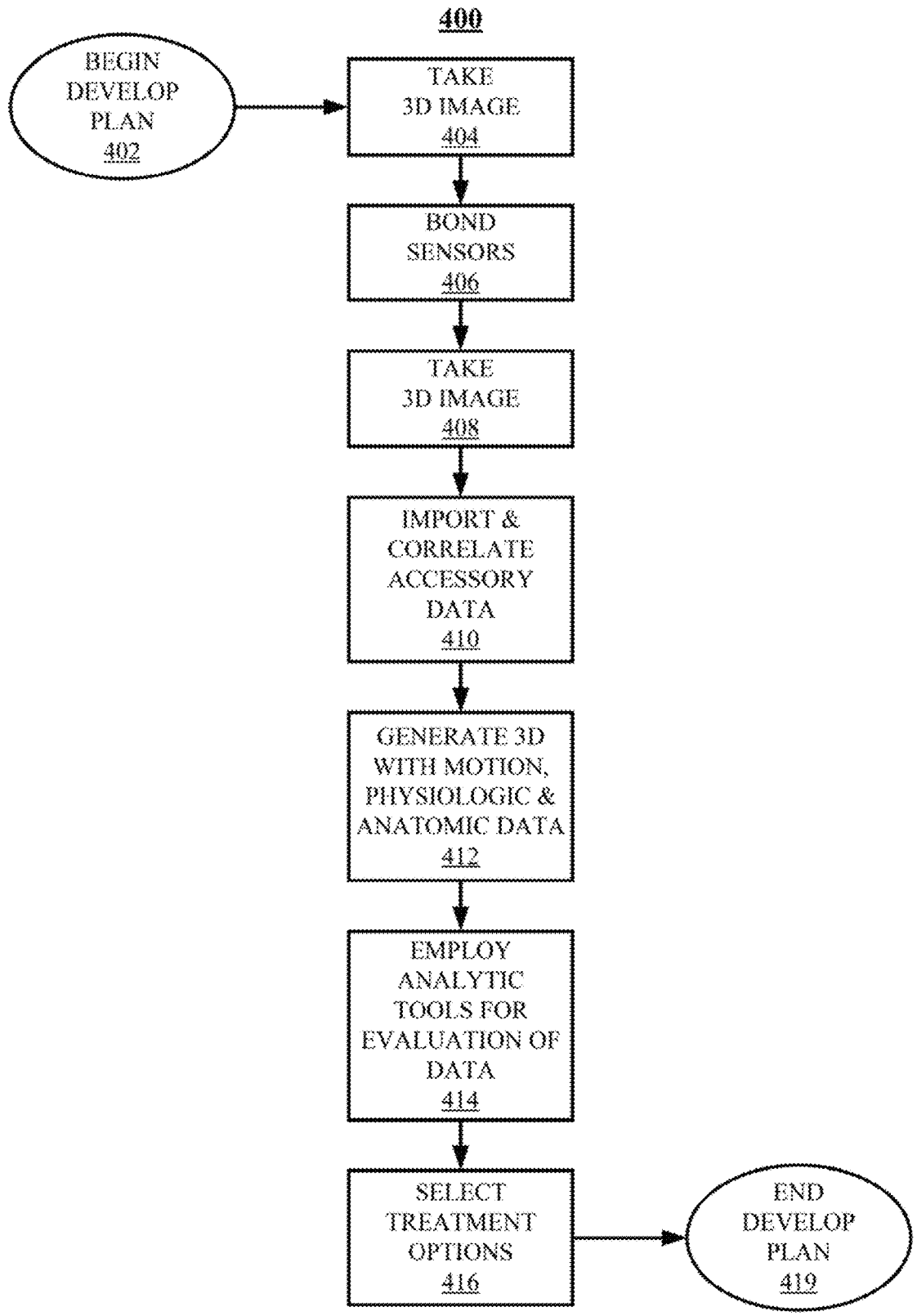
FIG. 9 is a flowchart of a "Plan Treatment" process that may implement aspects of the claimed subject matter.
Figure 10:
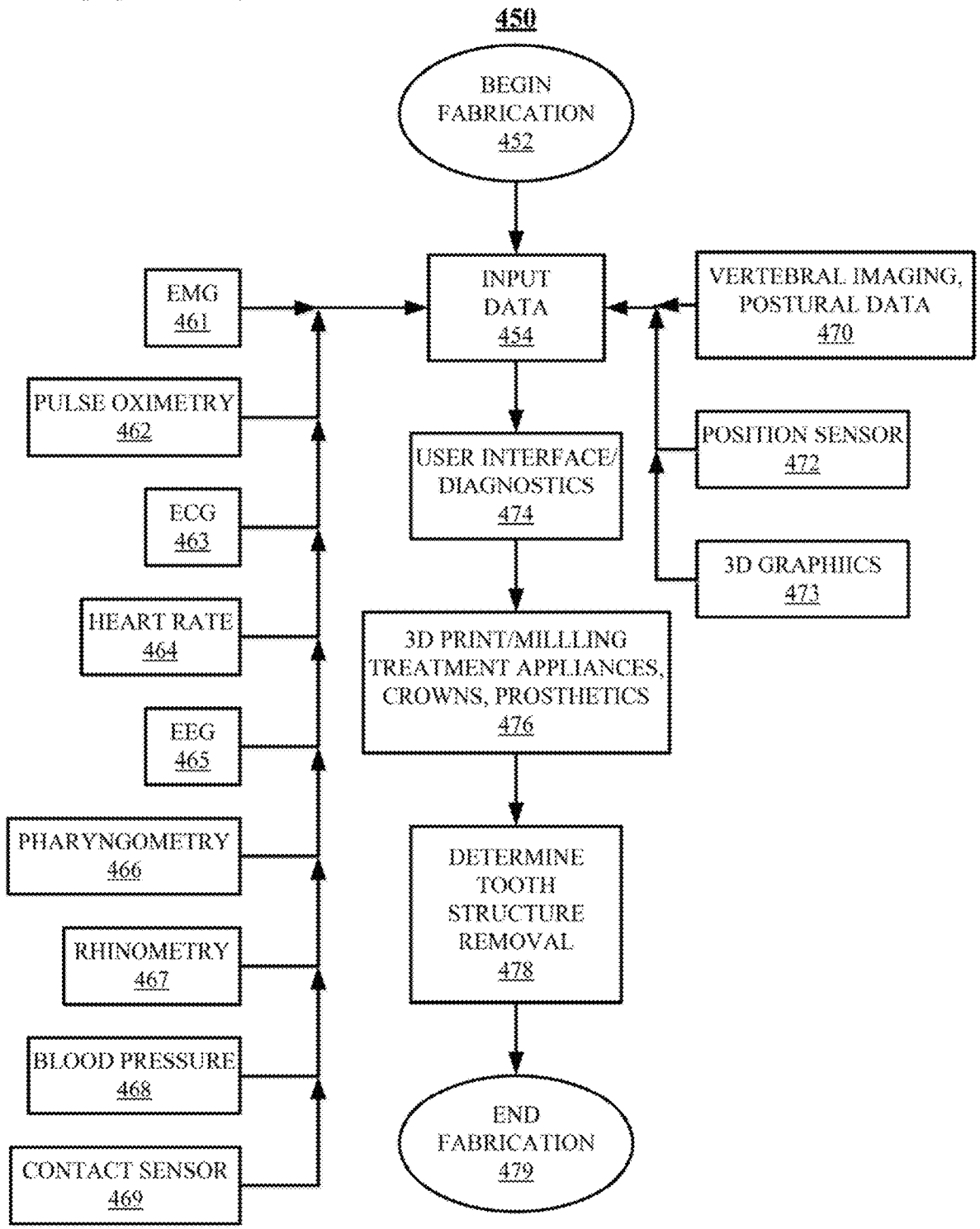
FIG. 10 is a flowchart of an "Implement Treatment" process that may incorporate aspects of the claimed subject matter.

Computing system 352 and CPU 354 are connected to a network 370, which is also connected to a data collection module 372, which represents the many different sources of information for the disclosed technology (see 461-470, 472 and 473, FIG. 10). Also coupled to network 370 are a 3D printer 374, milling tools 376 and 3D glasses 378. Although in this example, computing system 252 and data collection 372, 3D printer 374, milling tools 376 and eyeglasses 378 are communicatively coupled via network 370, they could also be coupled through any number of communication mediums such as, but not limited to, hard wires and the Internet (not shown). Further, it should be noted there are many possible computing system configurations, of which computing architecture 100 is only one simple example. The use of DGS 366, data collection 372, 3D printer 374, milling tools 376 are explained in more detail below in conjunction with FIGS. 9 and 10.

FIG. 9 is a flowchart of a "Develop Plan" process 400 that may implement aspects of the claimed subject matter. In this example, aspects of process 400 are associated with logic stored on CRSM 362 (FIG. 8) in conjunction with DIGS 366 (FIG. 8) and executed on one of more processors (not shown) of CPU 354 (FIG. 8) of computing system 352 (FIG. 8).

Processing starts in a "Begin Plan Treatment" block 402 and proceeds immediately to a "Take 3D Image" block 304. During processing associated with block 304, a 3D image of teeth/jaws 100 (FIG. 1-3) is taken. During processing associated with a "Bond Sensors" block 306, sensors (see 112, 116, FIGS. 1 and 150, FIG. 4) are attached to jaw/teeth 100 (FIGS. 1-3). During processing associated with a "Take 3D Image" block 406, 3D images of teeth/jaws 100 are acquired the sensors in place. In a single sensor arrangement, the teeth are 3D imaged with the teeth closed in a clench to calibrate the sensor to the closed position using graphic correlation.

During processing associated with an "Import and Correlate Accessory Data" block 410, any addition data from data sources (see 461-470, 472 and 473, FIG. 10) is collected and correlated with the 3D image data taken during processing associated with blocks 404 and 408. During processing associated with a "Generate 3D With Motion, Physiologic and Anatomic Data" block 412, the data collected and correlated during processing associated with block 410 is employed to generate 3D, physiologic and anatomic data. During processing associated with an "Employ Analytic Tools for Evaluation of Data" block 414, the data collected and correlated during processing associated with block 410 and the data generated during processing associated with block 412 are evaluated to determine possible treatment plans. During processing associated with a "Select Treatment Plan" block 416, a treatment plan identified during processing associated with block 414 is selected. Finally, processing proceeds to an "End Develop Plan" block 419 in which process 400 is complete.

FIG. 10 is a flowchart of an "Implement Treatment" process that incorporate aspect of the claimed subject matter. Like process 400, in this example, aspects of process 450 are associated with logic stored on CRSM 362 (FIG. 8) in conjunction with DIGS 366 (FIG. 8) and executed on one of more processors (not shown) of CPU 354 (FIG. 8) of computing system 352 (FIG. 8).

Processing starts in a "Begin Fabrication" block 452 and proceeds immediately to an "Import Data" block 452. During processing associated with block 452, data from accessory devices are imported into the system. Example of such devices include, but are not limited to, devices that generate or measure an electromyography (EMG) 461, a pulse oximetry 462, an electrocardiogram (ECG) 463, a heart rate 464, an electroencephalogram (EEG) 465, a pharyngometry 466, a rhinometry 467, blood pressure 468 and contact sensor data 469 and vertebral imaging, postural data 470. In addition, a position sensor 472 and 3D graphics 473 may be imported. In other words, data inputs of physiologic measurements 461-470 are fused with 3D imaging 473 and position sensor data 472.

During processing associated with a "User/Interface/Diagnostics" block 474, a user interface (not shown) is generated to display the data collected during processing associated with block 454. The rendering of data is comprehensively displayed to show a real-time or time-stamp correlation that allows one to see an anatomic model of jaw/teeth 100 (FIG. 1-3) in function. The user interface has diagnostic tools in the visualization rendering to aid in determining the correct craniomandibular relationship with six (6) degrees of freedom.

During processing associated with a 3D Printing/Milling Treatment Appliances, Crowns and Prosthetics" block 476, A CAD/CAM treatment solution is designed then fabricated either in office or in a lab with milling tools 376 (FIG. 8) or 3D printer 374 (FIG. 8). Treatment appliances may treat headaches, orthodontics, sleep apnea, TMJ dysfunctions and to prevent wear from grinding of the teeth. During processing associated with a "Determine Tooth Structure Removal" block 478, an exact and precalculated area of tooth structure to remove to achieve an ideal bite may be calculated. Augmented reality eyewear (ARE), such as ARE 378 (FIG. 8), may display an overlay of a digital treatment plan, including the visualization of tooth structure needed to be removed to achieve a desired shape of the tooth. The graphical display may appear within the eyewear over actual teeth to guide treatment.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements and/or additional, less or modified blocks performed in the same or a different order.

I claim:

1. A method adapted for enabling visualizing function of a jaw structure of a patient, comprising:

acquiring, by one or more processors of a computing system, 3-dimensional (3D) images of a jaw structure, wherein the jaw structure comprises an upper jaw and a lower jaw and wherein each of the 3D images depicting a respective position of the lower jaw relative to the upper jaw;

acquiring, by the one or more processors of the computing system, jaw position information characterizing positions of the lower jaw and the upper jaw, wherein the jaw position information is generated by a position sensor as a function of a reference signal emitted by a reference signal emitting device, wherein the position sensor is affixed to a first pair of adjacent teeth of the lower jaw, wherein the reference signal emitting device is affixed to a second pair of adjacent teeth of the upper jaw and wherein the position sensor and the reference signal emitting device are each affixed to a surface of the respective pairs of adjacent teeth for enabling teeth of the lower jaw and teeth of an upper jaw to be brought into direct contact with each other in an habitual bite configuration in a manner that is unaffected by the position sensor being affixed to the first pair of adjacent teeth of the lower jaw and the reference signal emitting device being affixed to the second pair of adjacent teeth of the upper jaw; and correlating, by the one or more processors of the computing system, the 3D images and the jaw position information to generate a 3D jaw motion model enabling visualization of the function of the jaw structure at least partially defined by motion of the lower jaw relative to the upper jaw between the habitual bite configuration and one or more open configurations.

2. The method of claim 1 wherein the 3D images includes:
a first set of images without the position sensor being affixed to the first pair of adjacent teeth of the lower jaw and without the reference signal emitting device being affixed to the second pair of adjacent teeth of the upper jaw; and
a second set of images with the position sensor being affixed to the first pair of adjacent teeth of the lower jaw and with the reference signal emitting device being affixed to the second pair of adjacent teeth of the upper jaw.

3. The method of claim 1 wherein the first and second pairs of adjacent teeth are located at a rear portion of the lower jaw.

4. The method of claim 1, wherein the position sensor and the reference signal emitting device are each bonded to surfaces of the respective pair of adjacent teeth.

5. The method of claim 4 wherein the position sensor and the reference signal emitting device each being bonded to the surfaces of the respective pair of adjacent teeth includes:
bonding the position sensor and the reference signal emitting device to the surfaces of the respective pair of adjacent teeth while the teeth of the lower jaw and teeth of the upper jaw are in the habitual bite configuration.

6. The method of claim 1 wherein the position sensor and the reference signal emitting device are each bonded to an outward facing surface of the respective pair of adjacent teeth for enabling the teeth of the lower jaw and the teeth of the upper jaw to be brought into direct contact with each other the habitual bite configuration in a manner that is unaffected by the position sensor being affixed to the first pair of adjacent teeth of the lower jaw and the reference signal emitting device being affixed to the second pair of adjacent teeth of the upper jaw.

7. The method of claim 1 wherein the position sensor comprises a magnetometer and the reference signal emitting device comprises a magnet.

8. The method of claim 1 wherein the one or more processors of the computing system acquiring the jaw position characterizing information includes the at least one of the position sensor or the reference signal emitting device wirelessly transmitting the jaw position characterizing information for reception by the computing system.

9. The method of claim 8 wherein the position sensor comprises a magnetometer and the reference signal emitting device comprises a magnet.

10. The method of claim 1, further comprising outputting, by the one or more processors of the computing system, information enabling the 3D jaw motion model to be visualized on a display device.

11. The method of claim 10 wherein the position sensor and the reference signal emitting device are each bonded to an outward facing surface of the respective pair of adjacent teeth for enabling the teeth of the lower jaw and the teeth of the upper jaw to be brought into direct contact with each other the habitual bite configuration in a manner that is unaffected by the position sensor being affixed to the first pair of adjacent teeth of the lower jaw and the reference signal emitting device being affixed to the second pair of adjacent teeth of the upper jaw.

12. The method of claim 10 wherein the one or more processors of the computing system acquiring the jaw position characterizing information includes the at least one of the position sensor or the reference signal emitting device wirelessly transmitting the jaw position characterizing information for reception by the computing system.

13. The method of claim 1, further comprising acquiring, by the one or more processors of the computing system, position information derived from a bilateral temporomandibular joint (TMJ) ultrasound, wherein said correlating includes correlating the said bilateral TMJ position information with the jaw position characterizing information.

14. The method of claim 13, further comprising outputting, by the one or more processors of the computing system, information enabling the 3D jaw motion model to be visualized on a display device.

15. An apparatus adapted for generating jaw motion information relating to an upper and lower jaw of a patient, comprising:
a reference signal emitting device affixed to a surface of a first pair of adjacent teeth of an upper jaw of a patient to permit the teeth of a lower jaw of the patient and the teeth of the upper jaw to be brought into direct contact with each other in a habitual bite configuration in a manner that is unaffected by the reference signal emitting device being affixed to the first pair of adjacent teeth;
a position sensor affixed to surface of a respective second pair of adjacent teeth of the lower jaw to permit the teeth of the lower jaw and the teeth of the upper jaw to be brought into direct contact with each other in the habitual bite configuration in a manner that is unaffected by each of the position sensor being affixed to the second pair of adjacent teeth of the lower jaw, wherein the position sensor is adapted to sense a reference signal emitted by the reference signal emitting device, to generate respective information characterizing position of the lower jaw relative to the upper jaw as a function of the reference signal and to transmit the jaw position characterizing information for reception by a remotely-located computing system.

16. The apparatus of claim 15 wherein the first and second pairs of adjacent teeth are at a rear portion of the lower jaw.

17. The apparatus of claim 15 wherein the position sensor and the reference signal emitting device are each bonded to surfaces of the respective pair of adjacent teeth.

18. The apparatus of claim 15 wherein:
the position sensor is affixed to an outward facing surface of the second pair of adjacent teeth; and
the reference signal emitting device is affixed to an outward facing surface of the first pair of adjacent teeth.

19. The apparatus of claim 15 wherein the position sensor comprises a magnetometer and the reference signal emitting device comprises a magnet.

20. The apparatus of claim 19 wherein the first and second pairs of adjacent teeth are at a rear portion of the lower jaw.

21. The apparatus of claim 20 wherein the position sensor and the reference signal emitting device are each bonded to surfaces of the respective pair of adjacent teeth.

22. The apparatus of claim 21 wherein:
the position sensor is affixed to outward facing surfaces of the second pair of adjacent teeth; and
the reference signal emitting device is affixed to outward facing surfaces of the first pair of adjacent teeth.

23. The apparatus of claim 15 wherein the position sensor is a wireless position sensor adapted for wirelessly transmitting the respective the jaw position characterizing information for reception by the remotely-located computing system.

24. The apparatus of claim 23 wherein the at least one position sensor comprises a magnetometer and the reference signal emitting device comprises a magnet.

25. The apparatus of claim 24 wherein the first and second pairs of adjacent teeth are at a rear portion of the lower jaw.

26. A sensor adapted to enable position information characterizing jaw function to be generated,
- a magnetometer outputting a position-determining information characterized by proximity to a source of a magnetic field;
- a signal transmitter that outputs a signal generated as a function of the position-determining information; and
- wherein the magnetometer and the signal transmitter are in the form of a unitary article enabling the sensor to be affixed to a first and second pairs of adjacent teeth, permitting teeth of the opposing jaws to be brought into direct contact with each other in a habitual bite configuration in a manner that is unaffected by the sensor being affixed to the first and second pairs of adjacent teeth.

27. The sensor of claim 26, further comprising a power source for providing electrical power to the magnetometer and to the signal transmitter, wherein the magnetometer, the signal transmitter and the power source are integrated for enabling the sensor to be affixed to surfaces of the first and second pairs of adjacent teeth for permitting teeth of the opposing jaws to be brought into direct contact with each other in the habitual bite configuration in a manner that is unaffected by the sensor being affixed to the tooth.

28. The sensor of claim 26 wherein the signal transmitter is a wireless signal transmitter.

29. The sensor of claim 28, further comprising a power source for providing electrical power to the magnetometer and to the signal transmitter, wherein the magnetometer, the signal transmitter and the power source are integrated for enabling the sensor to be affixed to surfaces of the first and second pairs of adjacent teeth for permitting teeth of the opposing jaws to be brought into direct contact with each other in the habitual bite configuration in a manner that is unaffected by the sensor being affixed to the tooth.

30. The sensor of claim 29 wherein the signal transmitter and the magnetometer are implemented as a radio transceiver micro controller with a magnetometer integral therewith.

\* \* \* \* \*